United States Patent
Xia et al.

(10) Patent No.: US 7,228,017 B2
(45) Date of Patent: Jun. 5, 2007

(54) FIBER OPTIC SENSING DEVICE AND METHOD OF MAKING AND OPERATING THE SAME

(75) Inventors: Hua Xia, Altamont, NY (US); Renato Guida, Wynantskill, NY (US); Kung Li Deng, Waterford, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/240,057

(22) Filed: Sep. 30, 2005

(65) Prior Publication Data
US 2007/0075225 A1    Apr. 5, 2007

(51) Int. Cl.
G02B 6/00    (2006.01)
G01J 1/04    (2006.01)
H01L 21/00   (2006.01)

(52) U.S. Cl. ............... 385/12; 385/37; 385/123; 385/124; 385/141; 250/227.11; 250/227.14; 250/227.18; 438/32

(58) Field of Classification Search ............... 385/12, 385/37, 123, 124, 141, 142, 143, 144; 250/227.11, 250/227.14, 227.18; 438/32
See application file for complete search history.

(56) References Cited

U.S. PATENT DOCUMENTS

| 5,168,156 A | 12/1992 | Fischer et al. ......... 250/227.21 |
| 6,072,922 A * | 6/2000 | Albin et al. .................. 385/12 |
| 6,950,578 B1 | 9/2005 | Ramachandran ............. 385/37 |
| 6,965,708 B2 * | 11/2005 | Luo et al. ...................... 385/12 |
| 7,031,571 B2 * | 4/2006 | Mihailov et al. ............. 385/37 |
| 2004/0184731 A1 * | 9/2004 | Mihailov et al. ............. 385/37 |
| 2005/0163424 A1 * | 7/2005 | Chen ............................. 385/37 |
| 2005/0232541 A1 * | 10/2005 | Mihailov et al. ............. 385/37 |
| 2006/0215959 A1 | 9/2006 | McCarthy et al. ........ 385/37 X |

FOREIGN PATENT DOCUMENTS

WO    WO0106279 A1    1/2001    ............... 385/37 X

OTHER PUBLICATIONS

Shiquan Tao et al., "Porous Solgel Fiber as a Transducer for Highly Sensitive Chemical Sensing", *Optics Letters*, vol. 27, No. 16, pp. 1382-1384, Aug. 15, 2002.

Masaru Mitsushio, et al., "Simplification and Evaluation of a Gold-Deposited SPR Optical Fiber Sensor", *Analytical Sciences*, vol. 20., pp. 689-694, Apr. 2004.

Jeffrey T. Remillard, et al., "Demonstration of a High-Temperature Fiber-Optic Gas Sensor Made With a Sol-Gel Process to Incorporate a Fluorescent Indicator", *Applied Optics*, vol. 38, No. 25, pp. 5306-5309, Sep. 1, 1999.

(Continued)

*Primary Examiner*—Brian M. Healy
(74) *Attorney, Agent, or Firm*—Ann M. Agosti; Patrick K. Patnode (57) ABSTRACT

A chemical sensing device comprises a fiber core and a fiber cladding. The fiber core comprises an index-modulated grating region having an apodized profile configured for increasing shedding of light into the fiber cladding, and the fiber cladding of the chemical sensing device is configured for reflecting at least some of the deflected light back towards the fiber core. The sensing device is applicable in methods and systems for sensing chemicals.

33 Claims, 8 Drawing Sheets

OTHER PUBLICATIONS

Istvan Szendro, "Art and Practice to Emboss Gratings into Sol-Gel Waveguides", *Proceedings of SPIE.*, vol. 4284, pp. 80-87, 2001.

Heather J. Patrick, et al., "Analysis of Response of Long Period Fiber Gratings to External Index of Refraction", *Journal of Lightwave Technology*, vol. 16, No. 9, pp. 1606-1612, Sep. 1998.

Rosane Falate, et al., "Petroleum Hydrocarbon Detection with Long Period Gratings", *Proceedings of SBMO/IEEE MTT-S IMOC*, pp. 907-910, 2003.

EPO Seach Report Dated Jan. 10, 2007.

* cited by examiner

FIBER OPTIC SENSING DEVICE AND METHOD OF MAKING AND OPERATING THE SAME

BACKGROUND

The invention relates generally to chemical sensing and more particularly to fiber grating-based chemical sensing devices, systems and methods.

Fiber optic sensing methods have advantages including flexibility, small size, negligible weight, passivity, and immunity to electromagnetic interference. These characteristics make fiber optic sensors ideally suited for monitoring dynamic chemical and physical processes that are associated with changes in environment. The cascading capability of fiber optic sensing enables a distributed sensing application for large-area infrastructure embodiments such as oil tanks, pipelines, and power grid utilities in which fiber optic chemical sensing devices are embedded in multiple locations, some of which may be otherwise inaccessible.

Various sensing devices have been used. For example, some chemical sensing embodiments depend on dye molecules that absorb a particular wavelength of light and re-emit the light a short time late at a longer wavelength. Other sensing devices are employed to detect chemical parameters such as pH-value or corrosion, toxic chemicals, organic and inorganic fouling, and metal ions in an industrial processing system. These chemical sensing devices typically include electrochemical sensors, surface plasma resonance sensors, and attenuated total reflection sensors. Most of these sensors are limited by the operational conditions in which the sensors are employed. For example, conventional optical and electrochemical sensing devices are often limited to relatively mild pH conditions and, as such, limited operational temperature ranges. More specifically, conventional devices are typically limited to a pH range from about 5 to about 11 and temperatures lower than about 100° C.

Several fiber optic-based chemical-sensing devices have been used with examples including chemically active tapered fiber tips, chemically active fiber bundle distal ends, and chemically active fiber cladding embodiments. These chemical sensing devices typically include fluorescent dye immobilized doping, chemical sensitive thin film coatings, or combinations thereof. Chemical sensing with these fiber devices is based either on the reflectance intensity or on the fluorescence intensity. However, it is difficult to use these fiber optic sensors as real-time monitoring sensing devices because the fluctuation of the light source and environmental sensitive fluorescent dye luminescence limit measurement accuracy.

It is difficult to identify different chemicals in an environment like a water exchanger, a pipeline, oil and gas storage tanks, or an industrial processing system. Further, for large scale systems, a relatively large number of discrete chemical sensors may be required to map characteristics such as the structural health condition, pH-value, metal ion concentration, or inorganic fouling and scaling. Discrete optical, electrochemical and fiber optic sensors may not be scalable to meet a desired spatial resolution that is beneficial for accurate mapping of system conditions.

Short-period fiber Bragg grating (FBG) sensing devices have been used for refractive index measurement, pH-value sensing, and chemical identification. These sensing devices are typically based on D-type fibers, cladding etched fibers, or side-polished fibers. Such sensors utilize a wavelength encoding within a core of the sensor to measure a parameter based upon a Bragg wavelength shift that is generated on illumination of the grating through an illumination source. Thus, environmental effects on the periodicity of the grating alter the wavelength of light reflected, thereby providing an indication of the environmental effect, such as, pH, salinity, or temperature, for example.

Conventional telecommunication type FBG sensing devices have very little sensitivity to chemicals because the evanescent wave field is confined inside the fiber core (at a distance of about one wavelength from the fiber core and cladding interface). In order to make such FBG sensing devices chemically active, the fiber is mechanically modified to have an asymmetrical shape such as a D-shape, or is polished on one side, or has cladding thinned by a hydrofluoric acid etching process for example. In these processes, the fiber gratings are carefully prepared by polishing, cleaving, chemical etching, or shape- or polarization-controlled fabrication processes to turn a conventional fiber into a chemical sensing device. Processes to modify either the fiber cladding thickness or the fiber shape are intended to expose the evanescent wave field of the fiber core mode to an external medium.

It is difficult to simultaneously detect multiple parameters, such as pH, salinity, corrosion, and temperature, through a single mechanically or chemically modified Bragg grating sensing device. Further, multiple spectral signals at different wavelengths may be required to separate the effect of multiple sensed parameters from one another. Such separation of sensed parameters is difficult and time-consuming. Additionally, it is particularly challenging to fabricate multiple sensors on a single fiber cable when chemical etching a fiber with an inscribed Bragg grating structure. In principle, these fiber optic sensors have potential distribution capability, but, as a practical matter, it is not an easy task to handle multiple delicate sensors. In addition, the weak mechanical strength due to the thinner fiber grating cladding thickness can create failure modes.

Fiber long-period grating (LPG) sensors have demonstrated high sensitivity to surrounding medium refractive index variations due to forward cladding modes and core mode coupling efficiency. In LPG-based chemical sensors, the light in the fiber core is shed into the fiber cladding region. The resultant transmission loss depends strongly upon surrounding medium refractive index. Despite the removal of the cladding etch requirement, it is difficult to distribute many LPGs in a common chemical sensing system due to cladding modes crossover. Typically, within a bandwidth of one hundred nanometers, for example, the number of the LPG sensors is limited because of the multiple transmission peaks from each LPG. More practical difficulty lies in the detection of the chemical while other environmental factors such as temperature are varying. The different temperature and chemical sensitivities of the transmission peaks make it difficult to distinguish the chemical signal from the environmental influence.

Although cladding modes numbers or crossover can be reduced for LPG sensors by chemical etching for a LPG-based sensing device, the same mechanical processing challenge occurs as that associated with mechanically modifying short-period FBGs.

BRIEF DESCRIPTION

It would be desirable to have a versatile technique for chemical sensing that is based on fiber gratings but does not require etching fiber cladding or mechanically modifying the fiber grating shape.

Briefly, in accordance with one embodiment, a chemical sensing device comprises a fiber core and a fiber cladding. The fiber core comprises an index-modulated grating region having an apodized profile configured for increasing shedding of light into the fiber cladding. The fiber cladding of the chemical sensing device is configured for reflecting at least some of the shed light back towards the fiber core.

In accordance with another embodiment, a chemical sensing method comprises: (a) providing a fiber core and a fiber cladding, wherein the fiber core comprises an index-modulated grating region having an apodized profile configured for increasing shedding of light into the fiber cladding, and wherein the fiber cladding is configured for reflecting at least some of the shed light back towards the fiber core; (b) transmitting a light through the grating region; (c) obtaining a signal representative of reflection of the light from or a transmission of light through the grating region; (d) monitoring amplitude and wavelength shift changes in the signal over time; and (e) using the monitored shift changes to detect the presence of a chemical.

In accordance with another embodiment, a chemical sensing system comprises: (a) a chemical sensing device comprising a fiber core and a fiber cladding, wherein the fiber core comprises an index-modulated grating region having an apodized profile configured for increasing shedding of light into the fiber cladding, and wherein the fiber cladding configured for reflecting at least some of the shed light back towards the fiber core; (b) a light source configured to illuminate the core; and (c) a detector configured to measure a signal representative of a transmission of the light through the grating region or a reflection of the light from the grating region.

In accordance with another embodiment, a chemical sensing probe comprises: (a) a chemical sensing device comprising a fiber core and a fiber cladding, wherein the fiber core comprises an index-modulated grating region having an apodized profile configured for increasing shedding of light into the fiber cladding, and wherein the fiber cladding is configured for reflecting at least some of the shed light back towards the fiber core; and (b) an optical reference sensing device configured for obtaining a reference signal representative of reflection of the light from or a transmission of light through the reference sensing device.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

A fiber grating device, without requiring cladding etching, can be used to sense chemical solvents, solutions, and vapors when configured to effectively shed more light energy from the fiber core into the fiber cladding. Apodizing refractive index modulation along the fiber axis, with a raised cosine or Gaussian profile for example, is an effective technique to turn a regular fiber grating, such as a fiber Bragg grating (FBG), into a highly sensitive chemical sensing device. The chemical sensing abilities of such a modulated FBG are mainly attributed to the interaction between the evanescent wave field of high-order cladding modes and external medium or chemicals. The resulting coupling between the cladding modes and fundamental mode enables such a FBG to have high sensitivity to a surrounding medium variation.

Figure 1:
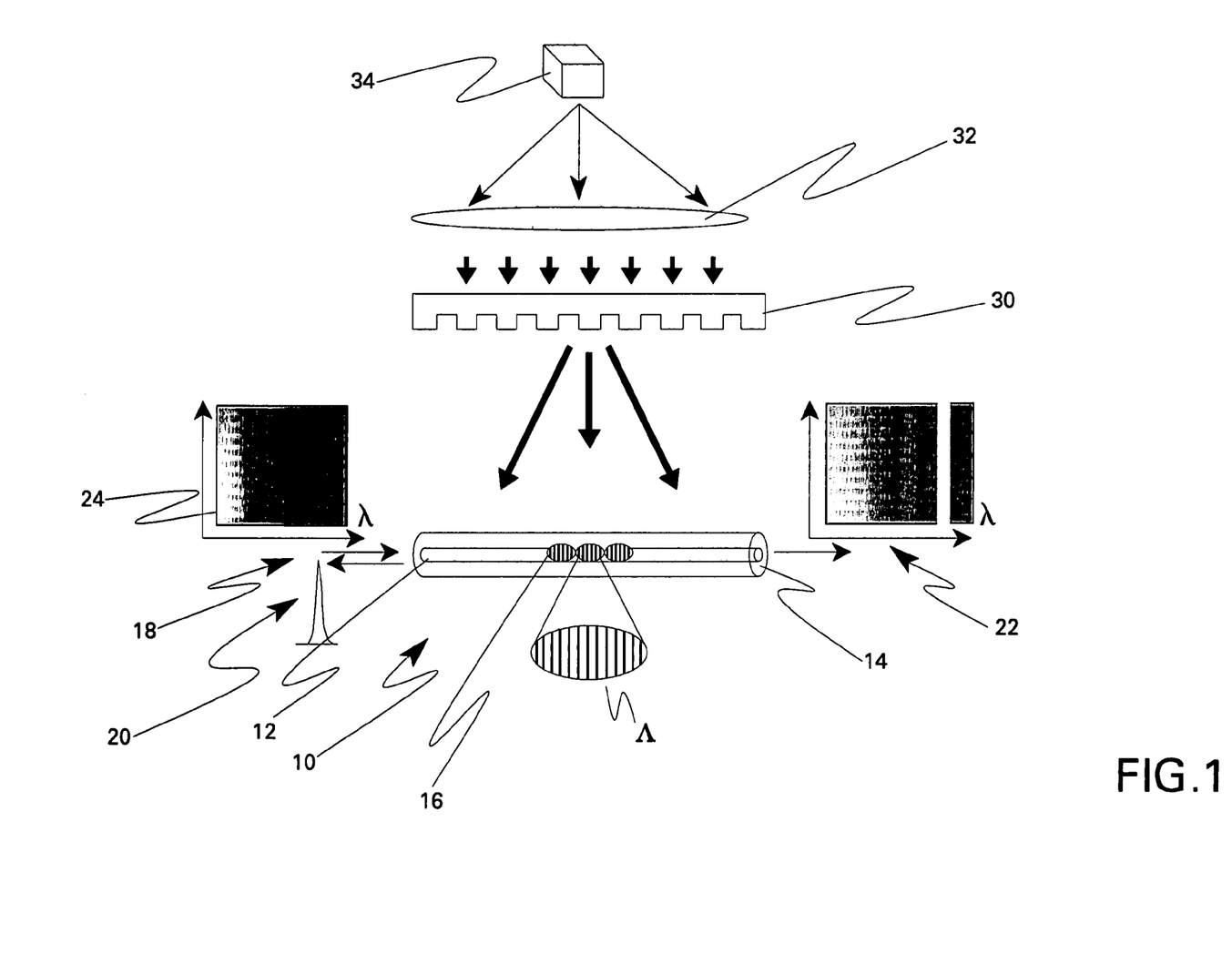
FIG. 1 is a perspective view of a chemical sensing device fabrication embodiment.

FIG. 1 is a perspective view of an system for fabricating a chemical sensing device 10 comprising a fiber core 12 and a fiber cladding 14. The fiber core comprises an index-modulated grating region 16 having an apodized profile configured for increasing shedding of light 18 into the fiber cladding, and the fiber cladding is configured for reflecting at least some of the shed light back towards the fiber core. As used herein "apodized profile" means that the refractive index is spatially modulated along the fiber axis. Typically the fiber cladding is configured for reflection by selection of the type of material (including whether it will have doping and, if so, what type), by design of the interface between the core and cladding, by design of the sensing surface, or combinations thereof. At least some of the light deflected back towards fiber core 12 (that is governed by Snell's law) is then combined with the signal (that is, the light going through the core without shedding). The types of chemicals which are intended to be encompassed within the chemical sensing device include chemical and biological gases and liquids for example.

Fiber core 12 typically comprises a single mode fiber core. In one example, fiber core 12 comprises germanium oxide co-doped with fluorine (F). The germanium is believed to increase photosensitivity, and the doping is believed to help minimize fiber core defects and light power loss. In addition to or instead of fluorine, other example dopant materials include chlorine (Cl), boron (B), phosphate (P), erbium (Er), and combinations thereof. Another potential core material comprises glass, for example. Fiber cladding 14 typically comprises doped silica or pure silicon dioxide (that is, silicon dioxide which has not been doped) a material which usually has a lower refractive index than the core. Fiber cladding 14 is typically in physical contact with fiber core 12.

Grating region 16 typically comprises a fiber Bragg grating. Any appropriate refractive index profile may be included with several non-limiting examples of apodized profiles being raised cosine apodized profiles and Gaussian apodized profiles. The sensing device may comprise multiple apodized profiles along the fiber axis.

EXAMPLE 1

In one fabrication method example, a modulated FBG based chemical sensing device has been fabricated with a strong 244 nanometer wavelength ultraviolet (UV) light 34 inscription by a lens 32 and periodic modulated phase mask 34. Before the grating inscription, a hydrogen loading process was used to enhance the fiber core 12 photosensitivity. Fiber core 12 was a single mode core with a diameter of about nine micrometers and co-doped by about five percent to about seven percent mole $GeO_2$ and about 10 ppm to about 100 ppm Fluorine. The combination of fiber cladding 14 and fiber core 12 was about 125 micrometers in diameter and without any doping elements. The refractive index modulation profile was apodized with a raised cosine pattern along the fiber axis.

A multiple apodization process can be used when the length of grating region 16 is larger than about 5 millimeter (mm). For example, several sequential apodization profiles are typically applied for a 36 mm length of fiber grating.

In a method of use embodiment, the chemical sensing device is used in a chemical sensing method which comprises transmitting a light through the grating region; obtaining a signal representative of reflection 20 of the light from or a transmission 22 of light through the grating region; monitoring amplitude and wavelength shift changes in the signal over time; and using the monitored shift changes to detect the presence of a chemical. As used herein "or" in the context of reflection or transmission means "either one alone or both." Part of light signal 24 is reflected from grating region 16 and rest of the light is transmitted through grating region 16 with, when the grating comprises a Bragg grating, a power loss in the wavelength corresponding to coherent Bragg resonance.

EXAMPLE 2

The sensing device described with respect to EXAMPLE 1 was illuminated by a near infrared broadband light source from a tunable laser diode, and the chemicals were detected by observing a time-dependent wavelength shift from an interrogation system in monitoring both reflectance and transmittance. The absorption processes of the target chemical modulate the fiber grating optical properties and thereby modulate the coupling properties between the cladding modes and fundamental mode. Chemical sensing based on this apodized FBG has experimentally shown perceivable Bragg resonant wavelength shift with 20–200 pm downshift and decay-like response characteristics from acetone, methanol, toluene, isopropyl alcohol, and hydrofluoric acid.

In a more specific method embodiment, the light comprises a test light and, prior to transmitting the test light, a training light is transmitted through grating region 16, a chemical (meaning at least one) is introduced into an environment of fiber core 12, a training signal representative of a reflection of the training light from or a transmission of the training light through grating region 16 is obtained; amplitude and wavelength shift changes are monitored in the signal over time; and the monitored shift changes in signal are used to form a look-up table for use when transmitting the test light. Moreover, chemical sensing device 10 may be self-calibrated either by the reflected peak position or by the dip position in the transmitted spectra (FIG. 1).

Figure 2:
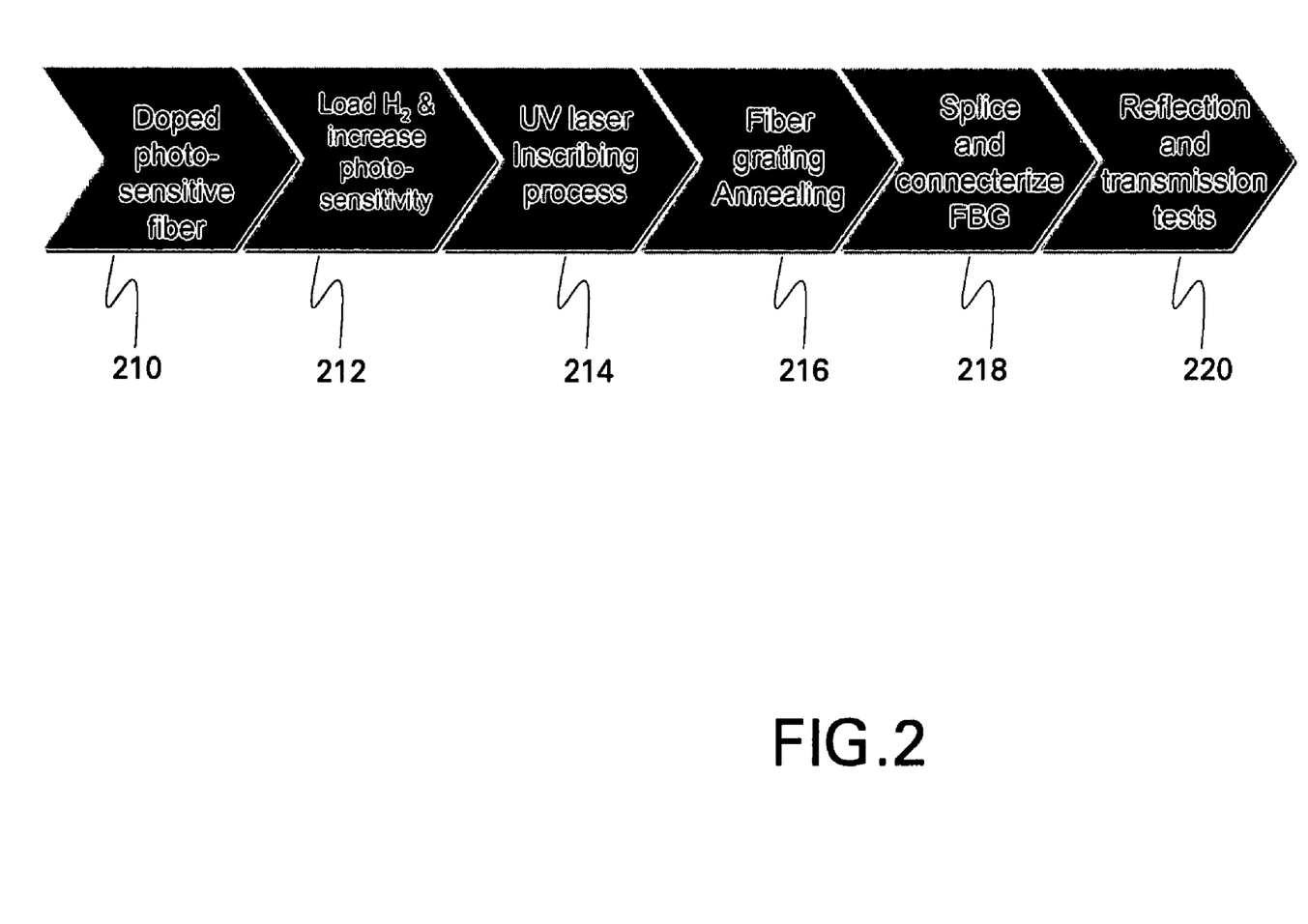
FIG. 2 is a diagram of a chemical sensing device fabrication process in accordance with another embodiment.

FIG. 2 is a flow diagram of a chemical sensing device fabrication process in accordance another embodiment. In step 210, a doped photo-sensitive fiber such as $GeO_2$ is provided. For simplifying the sensing signal interrogation, a single-mode fiber is typically used.

In step 212, hydrogen loading is performed. Such hydrogen loading increases the modulation and provides photo-sensitivity enhancement. In one example, hydrogen loading occurs for a period of time ranging from seven to ten days.

At step 214, a UV laser inscribing process occurs. Phase mask-based UV light interference is typically used to inscribe the grating region onto the fiber core.

Fiber annealing occurs at step 216. Annealing is useful to prompt hydrogen molecular out-diffusion. In one example, annealing occurs at a temperature of about 250° C. for a time of about 24 hours.

The thermally stabilized fiber is then connected and packed in step 218. Typically this includes attaching either a jacket cable or coating with a metal or polymer material such as aluminum, gold, copper, polyimide, or acrylate. A final spectral characterization can be performed at step 220 to check the line width of the reflected peak, Bragg resonant wavelength, and transmission dip and power loss aspects.

Figure 3:
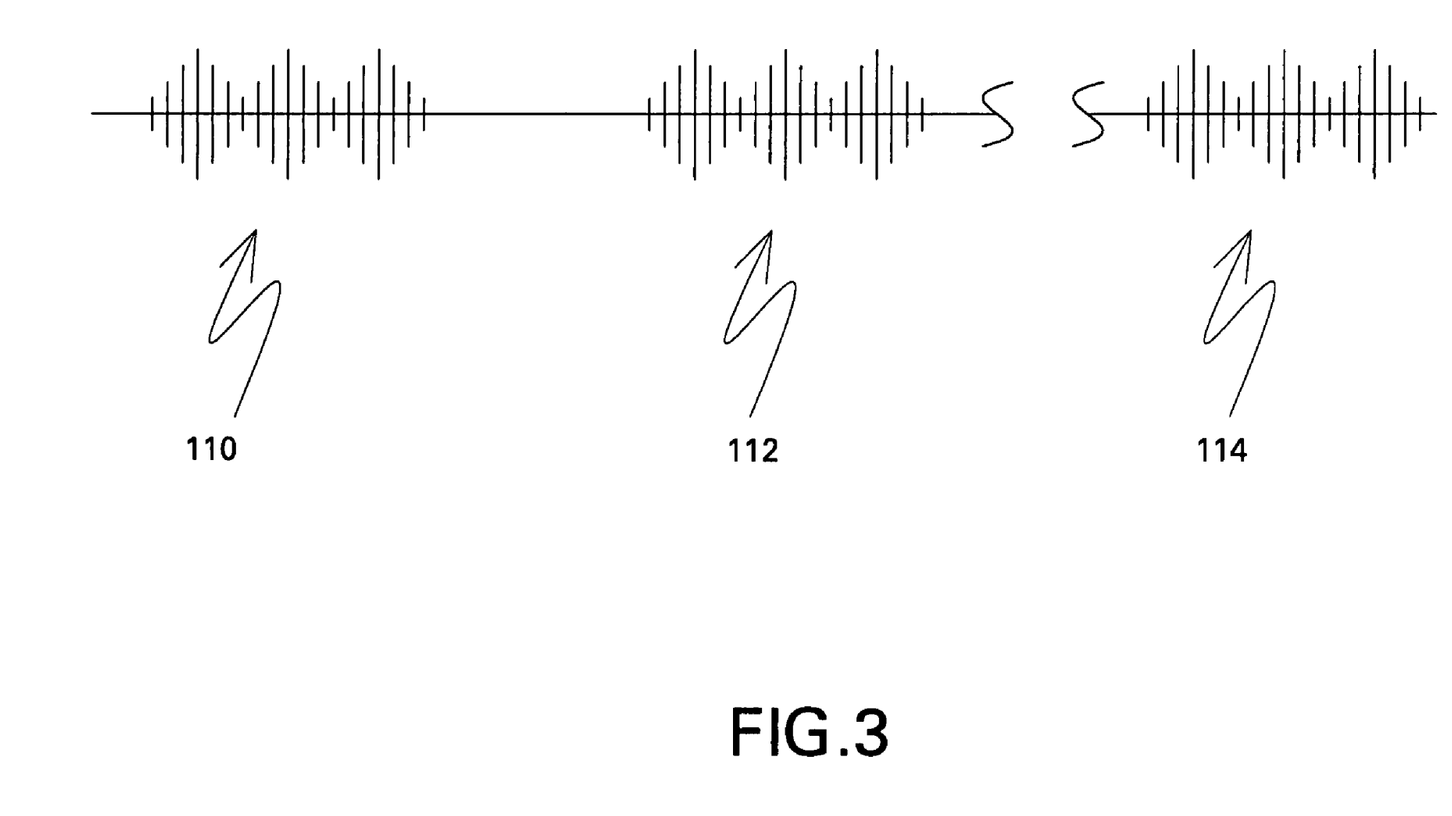
FIG. 3 is a schematic view of a plurality of chemical sensing devices with a raised cosine modulation profile along the fiber axis in accordance with another embodiment.

FIG. 3 is a schematic view of a plurality of chemical sensing devices 110, 112, and 114 in accordance with another embodiment of the present invention. Such embodiments can be used to either sense the same parameter at different locations or to sense multiple parameters at similar or different locations. For example, the observed wavelength shift and response time are two parameters for identifying different chemicals species regardless of temperature variation and other spurious events. The sensing devices of FIG. 3 may be configured on a common fiber core or may be on separate fiber cores that are coupled in series. Still another alternative embodiment, not shown, is to have some or each of the sensing devices in parallel along different fibers.

Figure 4:
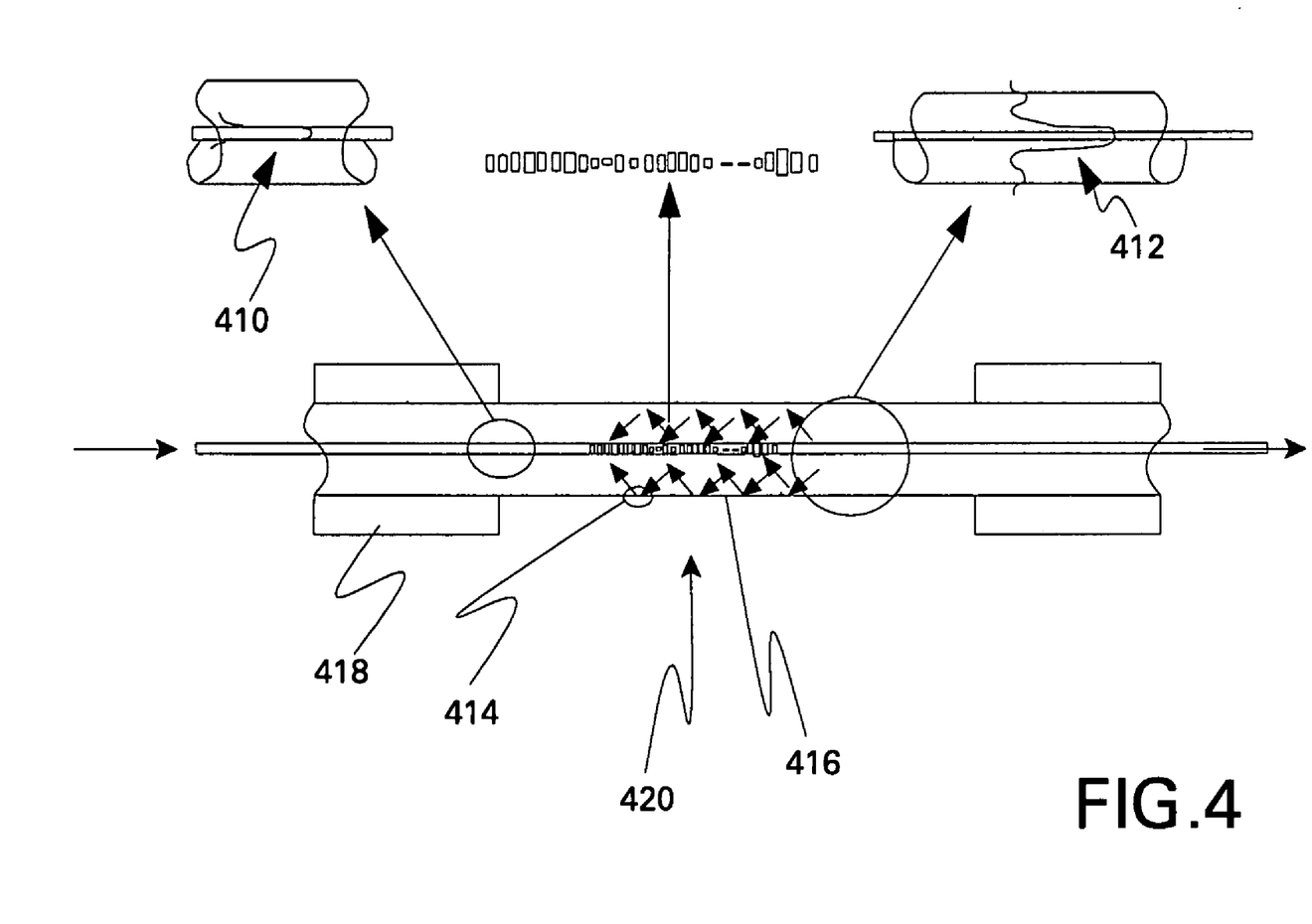
FIG. 4 is a schematic view of evanescent wave field profiles on opposing sides of a refractive index grating having an apodized profile.

FIG. 4 is an example view of evanescent wave field profiles on opposing sides of chemical sensing device 420 which has an index-modulated grating region having an apodized profile. Prior to passing through the grating region, the wave packet profile is a confined evanescent wave field 410 of the fundamental mode. After passing through the grating region, the wave packet profile is an extended high-order mode involved wave packet 412. The chemical sensing effect of embodiments described herein is believed to be due to the interaction between the evanescent wave field of the high-order cladding modes and the external medium or chemicals. The refractive index of the external medium or chemical modifies the solid (fiber cladding) and liquid (chemical) boundary condition 416 so that the coupling of the reflected high-order cladding modes and fundamental mode depends strongly upon the chemical affinity, interfacial free energy and its relaxation process. The part of the high-order cladding modes that is refracted (shown by area 414) from the sensing surface is governed by Snell's law. Additionally, the excited high-order cladding modes are partially reflected (back towards the core) in the sensing subsurface. FIG. 4 additionally illustrates a coating 418 encasing areas of the fiber other than the grating region of chemical sensing device 420.

Figure 5:
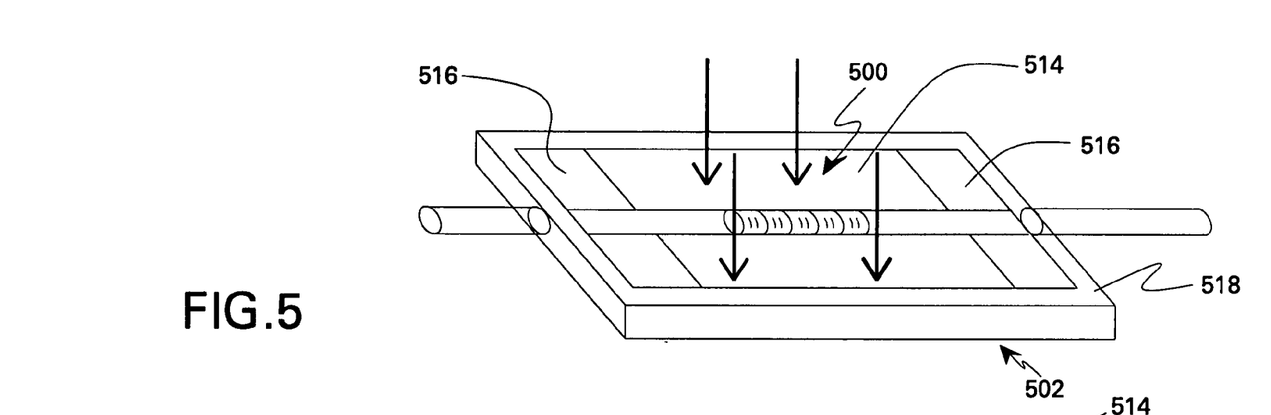
FIG. 5 is a schematic view of a single device based sensing probe.
Figure 6:
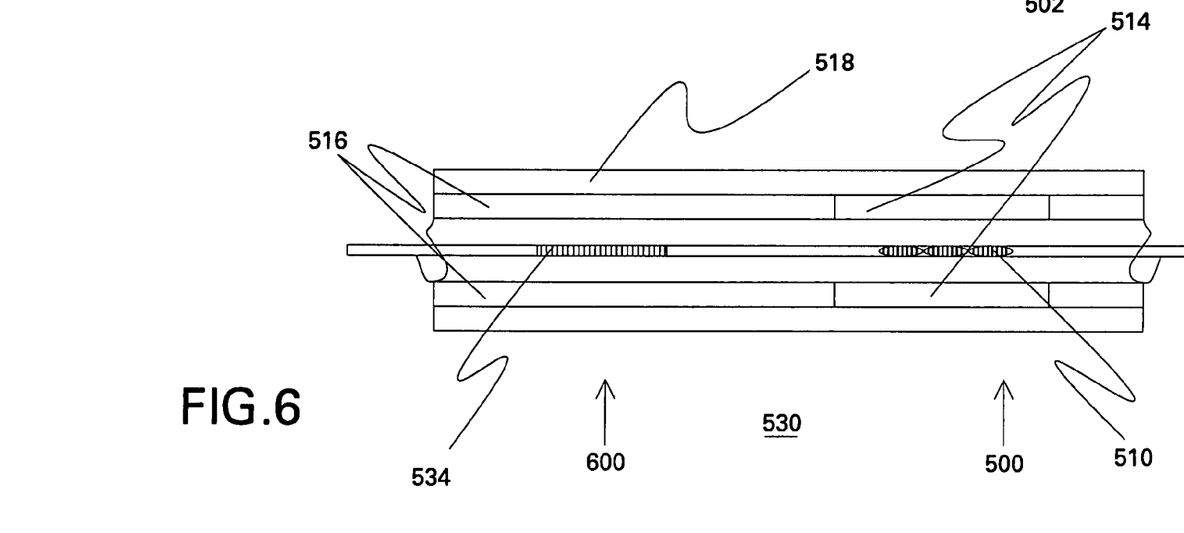
FIG. 6 is a schematic view of a multi-device based sensing probe.

FIGS. 5 and 6 schematically illustrate two chemical sensing probes with FIG. 5 being a perspective view and FIG. 6 being a top view. Single device probe 502 of FIG. 5 comprises a chemical sensing device 500 of the type described with respect to FIG. 1 including a fiber core, fiber cladding, and index-modulated grating region having an apodized profile (shown in FIG. 1). FIG. 5 additionally illustrates a free sensing space 514 situated over at least a portion of the fiber cladding which surrounds the grating region, coated layer 516 comprising a material such as a polymer or metal, and fiber sensing device package 518 encasing the entire assembly.

The two device probe 530 of FIG. 6 comprises a reference sensing device 600 including a reference grating 534 in addition to the elements of probe 502. A coating 516 such as a metal or polymer on the reference sensing device 600 provides fiber protection and may enhance environmental factor measurement accuracy.

Figure 7:
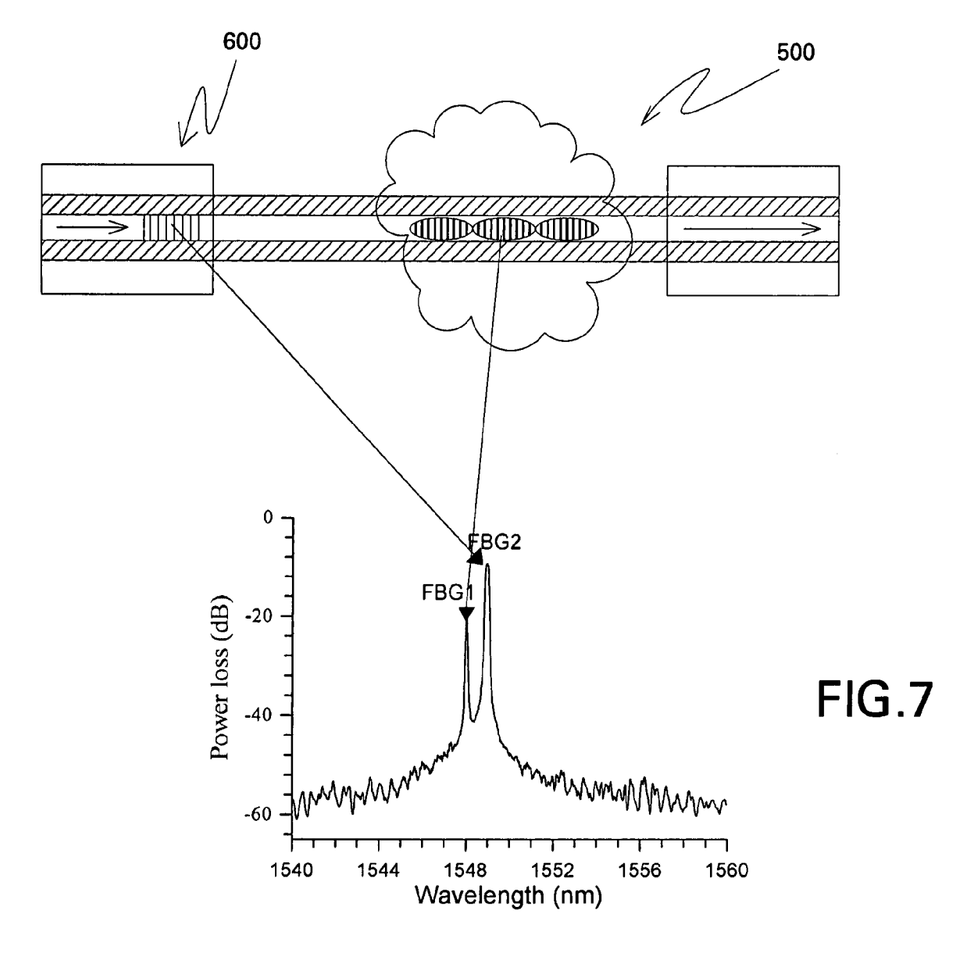
FIG. 7 is a schematic view of a chemical sensing embodiment in which an optical reference sensing device has a higher Bragg resonant wavelength than that of a chemical sensing device.

FIG. 7 further illustrates a design based on sensing devices 500 and 600. In the example of FIG. 7, the chemical sensing device 500 has a Bragg resonant wavelength from about two nanometers to about five nanometers lower than that of the reference sensing device 600 so that chemical related wavelength shift and reference related wavelength shift from the two sensing devices are opposite, and peak overlapping is avoided along with interference between the two grating regions while spacing between the two grating regions is less than 100 mm. This facilitates separation of the environmental influences (via one or more reference signals) of the temperature, corrosion, pH, pressure, and/or strain from the chemical sensing by comparing reflectance or transmittance variations in grating regions of the sensing devices.

If desired, a plurality of such pairs of devices can be combined into a distributed sensing system for multiple points of chemical identification in a temperature and humidity variable environment. The chemical sensing system may include, for example, a plurality of sensing devices disposed on a fiber cable that may span a few miles wherein each of the chemical sensing probes comprises a pair of fiber grating sensing devices with one having a bared grating region surface for maximum chemical interaction and the other having a coating thereon with a resonant wavelength higher than that of the bared sensing device.

Figure 8:
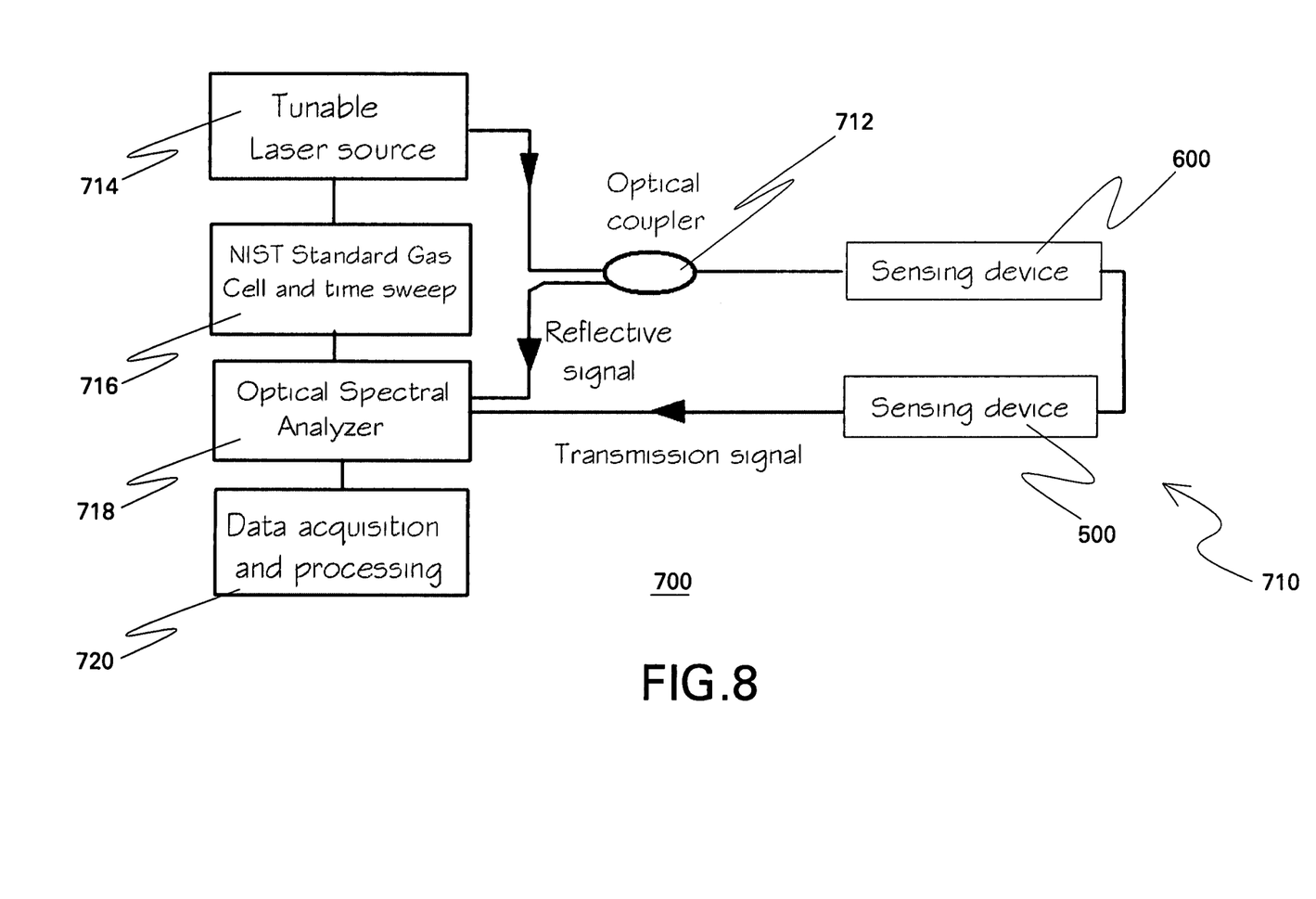
FIG. 8 is a diagrammatical representation of a fiber optic chemical sensing system for identifying a chemical operated either in reflection mode or transmission mode.

FIG. 8 is a block diagram illustrating a chemical sensing system 700 in accordance with another embodiment of the present invention wherein a probe 710, comprising a chemical sensing device 500 and a reference sensing device 600 of the type described above with respect to FIG. 6, is used in combination with a light source 714 configured to illuminate fiber core 12 (FIG. 1) and an optical spectral analyzer 718 configured to measure a signal representative of a transmission of the light through the probe or a reflection of the light from the probe. In one example, the light source comprises a broadband light source. In another example, the light source comprises a tunable laser light source with a wavelength from about 1450 nm to about 1600 nm. The system typically also includes a processor 720 configured for monitoring amplitude and wavelength shift changes in the signal over time and using the monitored shift changes to detect the presence of a chemical. A NIST standard gas cell 716 may simultaneously be used for obtaining absolute wavelength readings from each sensing device. The laser light is typically coupled into the fiber core and sensing device by an optical coupler 712.

Light coupling and signal pickup can be achieve by either an optical coupler or an optical circulator, for example, that is used to send the light source to sensing devices and, in return, couple the reflected or transmitted signal back to a signal interrogator such as optical spectral analyzer 718. The signal interrogation may be based a tunable Fabry-Perot filter and an indium gallium arsenide based near infrared photodetector that is configured to measure a signal representative of a transmission of the light through the fiber grating region or a reflection of the light from the fiber grating region.

Such coupling may optionally be on a common fiber core 12 (FIG. 1). Optical reference sensing device 600 comprises, in one embodiment, for example, a temperature sensing device that is designed so as to have minimal interaction with the chemical to be sensed and instead have a wavelength peak with any shift ($\Delta\lambda_1$) being primarily due to temperature changes. In contrast, the shift in the wavelength peak of the chemical sensing device 500 ($\Delta\lambda_2$) will be due to both temperature changes and chemical changes. The difference between the two peak shifts ($\Delta\lambda_2 - \Delta\lambda_1$) can be empirically determined, for example, at different chemical concentrations during a training mode and stored in a look-up table (as discussed above) for use and comparison during an operational mode.

EXAMPLE 3

For verification, a sensing system was fabricated and included chemical sensing device 500, a polyimide recoated fiber Bragg grating as a real-time temperature sensing device 600, and a four channel interrogation system 718. A one-milliwatt tunable diode laser 714 was connected to the sensing fiber through a fiber optic coupler 712. The scanned wavelength, with a rate of 80 nanometers per second, was calibrated with a gas cell and sweep meter 716. The system resolution was 0.4 pm for chemical sensing device 500 sensing. A tracking algorithm in processor 720 for transmission-dip and reflected peak was used to record the time-dependent chemical sensing. Care was taken to maintain the gratings with a proper tensile stress during the measurements by maintaining the sensing probe 710 with a stable support structure or package 518 (FIG. 6).

As part of chemical sensing probe 710, two fiber Bragg gratings were inscripted on a germanium oxide doped photosensitive silica single-mode fiber with a hydrogen loading process as discussed above with respect to EXAMPLE 1. In order to enhance the sensitivity of chemical sensing probe 710 to the surrounding medium or make the light propagated in the fiber core more loosely confined so that a large proportion of light propagates in the cladding, the UV light intensity was modulated during the grating inscripting process and shifted along the fiber axis. Such a modulated Bragg grating structure with apodized profile along the fiber axis resulted in a significant transmission dip that apparently arose from coupling the forward propagating fundamental mode with a counter-propagating mode in the core. In addition, because of the light coupled from the core mode leaking out the fiber core, several transmission dips were left due to the cladding modes resonance in the range of shorter wavelength than the Bragg resonant wavelength. It has been found that the number and the amplitude of these resonances depend on the UV light power level and fiber photosensitivity, as well as the optical properties of the fiber core/cladding interface.

A theoretical analysis on a strongly periodic refractive index modulation has been developed in which the modulation contribution from high-order propagation modes has been used to explain the observed chemical sensing results. It is believed that the chemical sensing is a process due to chemical atomic absorption around the grating surface that strongly modifies the mode coupling properties of the high-order cladding modes and fundamental mode, instead of the refractive index matching effect. Theoretically, this perceivable wavelength shift is attributed to the high-order modes contribution in which the coupling properties are modified by absorbed chemical atoms or molecules. Under the theoretical analysis, a Bragg resonant condition, for example, is expressed as:

$$\lambda_B = 2\bar{n}_{\mathit{eff}}\Lambda\delta(k, k_o) + (n_a - n_b)\Lambda \sum_{m\neq 0} \frac{2}{m\pi}\delta(k, k_m)e^{-i\frac{\pi m d_1}{\Lambda}}\sin\left(\frac{\pi m d_1}{\Lambda}\right), \quad (1)$$

wherein $d_1(d_2)$ is the UV exposed (unexposed) width on the fiber, $\Lambda$ is the pitch size, and the wave vector $k_m = 2\pi m/\Lambda$, for $m=0, 1, 2 \ldots$. The first term in Equation (1) corresponds to phase match condition for a FBG, and the $\bar{n}_{\mathit{eff}}$ is the effective refractive index of the fiber grating. For a regular fiber Bragg grating it is an effective refractive index of the fiber core, expressed by $\bar{n}_{\mathit{eff}} = f_A n(UV+GeF:SiO_2) + f_B n(GeF:SiO_2)$, where $f_A + f_B = 1$, and $f_A(f_B)$ is the ratio of the UV exposed (unexposed) fiber core width $d_1(d_2)$ to the pitch size $\Lambda$. Within first order approximation, a change of the external medium index is not perceivable where the high-order modes coupling contribution is very small. For a strongly modulated FBG, the resonant wavelength can be determined using the phase matching condition of $\beta_{clad,i} + \beta_{01} = 2\pi m/\Lambda$, where $\beta_{clad,i}$ is the propagation constant of the ith cladding in the opposite direction to the fundamental $LP_{01}$ mode with wave vector $\beta_{01}$, namely by $\lambda = (n_{co} + n_{clad,i})\Lambda$.

The high-order modes coupling effect in Equation (1) has not been realized and explored so far, particularly in the context of chemical sensing. The coupling of these high-order modes to counter-propagating fundamental mode, as a small perturbation, is expected to be a perceivable effect that can be used to sense chemicals and volatile vapors by present interrogation system with a 0.4 pm resolution and accuracy of 1 pm.

Figure 9:
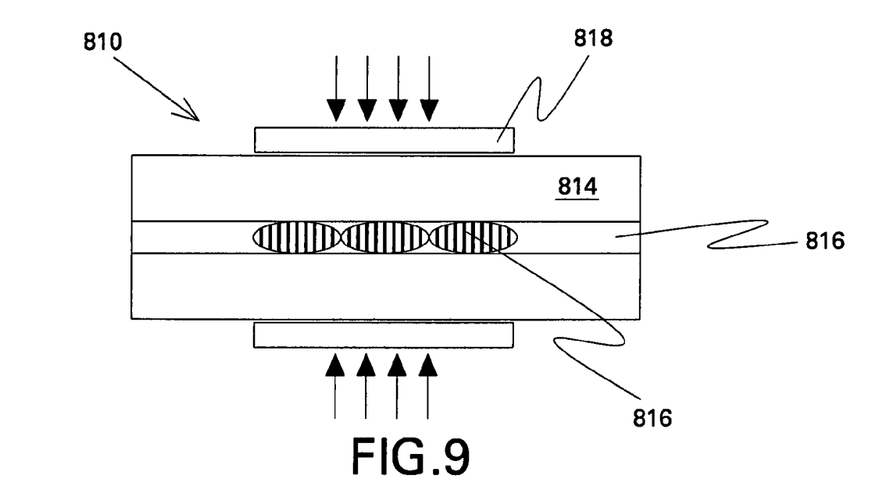
FIG. 9 illustrates one embodiment of a coated fiber grating.

It is expected that using optional selected coatings can further modify properties of the sensing devices. For example, in one embodiment, as shown in FIG. 9, a chemical selectivity coating 818 is situated over at least a portion of fiber cladding 814 of sensing device 810 which surrounds the grating region 816 of the fiber core 812. In a more specific embodiment, the coating comprises a polymer such as a polyimide or an acrylate.

Figure 10:
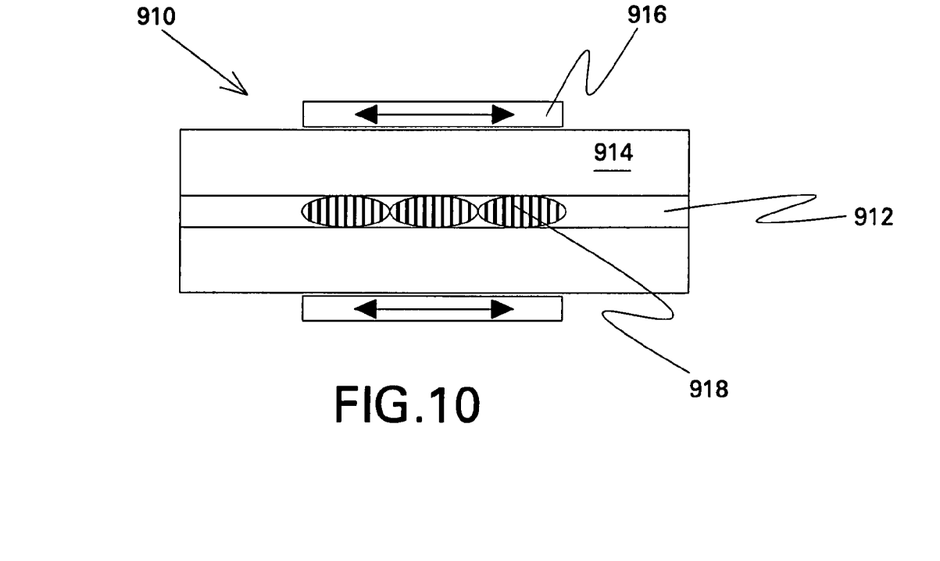
FIG. 10 illustrates another embodiment of a coated fiber grating.

In another embodiment, as shown in FIG. 10, a mechanical sensitivity coating 916 is situated over at least a portion of fiber cladding 914 which surrounds grating region 918 of fiber core 912. In a more specific variation, the mechanical sensitivity coating comprises a material with a coefficient of thermal expansion different than a coefficient of thermal expansion of the fiber cladding. In one example wherein the fiber cladding comprises silica, the coating comprises copper, aluminum, or gold. The coefficient of thermal expansion of aluminum, for example, is nearly 40 times higher than that of silica.

The choice of the fiber cladding material itself and any coating will depend upon optical properties as well as any requirements from the intended environment (for example impermeability or hydrophilicity if the sensing devices are to be used in certain gas or liquid environments). Gold metal coating material can be used for protection purposes and also can withstand temperatures up to about 600° C. Acrylate coated fibers are typically suitable for temperatures from about −40° C. to about 85° C., and polyimide coated fibers are generally suitable for temperatures from about −190° C. to about 350° C. Careful selection of a coating for the reference sensing device is also useful. For an example, polyimide coating can assist in sensing humidity variation whereas a copper metal-coated sensing device will help sense oxidization related corrosion.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A chemical sensing device comprising:
    a fiber core; and
    a fiber cladding,
    wherein the fiber core comprises an index-modulated grating region having an apodized profile configured for increasing shedding of light into the fiber cladding;
    wherein the fiber cladding of the chemical sensing device is configured for reflecting at least some of the shed light back towards the fiber core.

2. The sensing device of claim 1 wherein the fiber core comprises a single mode fiber core, and wherein the fiber core comprises a material doped with germanium dioxide.

3. The sensing device of claim 2 wherein the fiber core further comprises a material co-doped with fluorine, chlorine, boron, erbium, or combinations thereof.

4. The sensing device of claim 3 wherein the fiber cladding material comprises pure silicon dioxide.

5. The sensing device of claim 1 wherein the fiber cladding is in physical contact with the fiber core.

6. The sensing device of claim 1 wherein the profile of the grating region comprises a periodic apodized refractive index profile.

7. The sensing device of claim 6 wherein the profile of the grating region comprises at least one raised cosine profile along an axis of the fiber core.

8. The sensing device of claim 6 wherein the profile of the grating region comprises at least one Gaussian profile along an axis of the fiber core.

9. The sensing device of claim 1 further comprising a chemical selectivity coating situated over at least a portion of the fiber cladding which surrounds the grating region of the fiber core.

10. The sensing device of claim 9 wherein the chemical selectivity coating comprises a polymer.

11. The sensing device of claim 10 wherein the polymer comprises a polyimide or an acrylate.

12. The sensing device of claim 1 further comprising a mechanical sensitivity coating situated over at least a portion of the fiber cladding which surrounds the grating region of the fiber core.

13. The sensing device of claim 12 wherein the mechanical sensitivity coating comprises copper, aluminum, or gold.

14. The sensing device of claim 11 wherein the mechanical sensitivity coating comprises a material with a coefficient of thermal expansion different than a coefficient of thermal expansion of the fiber cladding.

15. A chemical sensing method comprising:
    providing a fiber core and a fiber cladding, wherein the fiber core comprises an index-modulated grating region having an apodized profile configured for increasing shedding of light into the fiber cladding, and wherein the fiber cladding is configured for reflecting at least some of the shed light back towards the fiber core;
    transmitting a light through the grating region;
    obtaining a signal representative of reflection of the light from or a transmission of light through the grating region;

monitoring amplitude and wavelength shift changes in the signal over time; and using the monitored shift changes to detect the presence of a chemical.

16. The method of claim 15 wherein obtaining the signal comprises obtaining a first signal representative of the reflection of the light from the grating region and a second signal representative of the transmission of light through the grating region.

17. The method of claim 15 wherein the signal comprises a chemical signal and further comprising providing an optical reference sensing device, obtaining a reference signal representative of reflection of the light from or a transmission of light through the reference sensing device, monitoring amplitude and wavelength shift changes in the reference signal over time; and using both the monitored chemical signal shift changes and the monitored reference signal shift changes to detect the presence of the chemical.

18. The method of claim 15 wherein the light comprises a test light and further comprising, prior to transmitting the test light, transmitting a training light through the grating region, introducing a chemical into an environment of the fiber core, obtaining a training signal representative of a reflection of the training light from or a transmission of the training light through the grating region;

monitoring amplitude and wavelength shift changes in the training signal over time; and using the monitored shift changes in training signal to form a look-up table for use when transmitting the test light.

19. The method of claim 15 wherein the grating region comprises a fiber Bragg grating and wherein the apodized profile comprises a raised cosine profile.

20. A chemical sensing system comprising:

a chemical sensing device comprising a fiber core and a fiber cladding, wherein the fiber core comprises an index-modulated grating region having an apodized profile configured for increasing shedding of light into the fiber cladding, and wherein the fiber cladding of the chemical sensor is configured for reflecting at least some of the shed light back towards the fiber core;

a light source configured to illuminate the core;

a detector configured to measure a signal representative of a transmission of the light through the grating region or a reflection of the light from the grating region.

21. The system of claim 20 further comprising a processor configured for monitoring amplitude and wavelength shift changes in the signal over time and using the monitored shift changes to detect the presence of a chemical.

22. The system of claim 21 wherein the fiber core comprises a single mode fiber core, and wherein the fiber core comprises germanium oxide doped with fluorine, chlorine, boron, erbium, or combinations thereof.

23. The system of claim 22 wherein the fiber cladding material comprises silicon dioxide.

24. The system of claim 21 wherein the apodized profile comprises a raised cosine or a Gaussian apodized profile.

25. The system of claim 21 wherein the chemical sensor comprises a plurality of chemical sensing devices.

26. The system of claim 25 wherein the chemical sensing devices are situated along the fiber core.

27. The system of claim 21 further comprising an optical reference sensing device configured for obtaining a reference signal representative of reflection of the light from or a transmission of light through the optical reference sensing device.

28. The system of claim 27 wherein the optical reference sensing device comprises a fiber grating temperature sensor coupled in parallel with the chemical sensing device.

29. A chemical sensing probe comprising:

a chemical sensing device comprising a fiber core and a fiber cladding, wherein the fiber core comprises an index-modulated grating region having an apodized profile configured for increasing shedding of light into the fiber cladding, and wherein the fiber cladding is configured for reflecting at least some of the shed light back towards the fiber core; and an optical reference sensing device configured for obtaining a reference signal representative of reflection of the light from or a transmission of light through the reference sensing device.

30. The probe of claim 29 wherein the fiber core comprises a core common to both the chemical sensing device and the optical reference sensing device.

31. The system of claim 29 wherein the fiber core comprises doped germanium oxide co-doped with fluorine, chlorine, boron, erbium, or combinations thereof, and wherein the fiber cladding material comprises silicon dioxide.

32. The system of claim 29 wherein the optical reference sensing device comprises a fiber grating temperature sensing device coupled in parallel with the chemical sensing device.

33. The system of claim 29 wherein the optical reference sensing device comprises a temperature sensing device, a corrosion sensing device, a pH sensing device, or combinations thereof.

* * * * *